United States Patent [19]

Moore

[11] 4,220,606

[45] Sep. 2, 1980

[54] CYCLIC HYDROCARBON PERFLUORINATION PROCESS

[75] Inventor: Robert E. Moore, Wilmington, Del.

[73] Assignee: Suntech, Inc., Philadelphia, Pa.

[21] Appl. No.: 54,332

[22] Filed: Jul. 2, 1979

Related U.S. Application Data

[63] Continuation-in-part of Ser. No. 968,942, Dec. 13, 1978, abandoned, which is a continuation of Ser. No. 898,058, Apr. 20, 1978, abandoned, which is a continuation-in-part of Ser. No. 771,873, Feb. 25, 1977, abandoned, which is a continuation-in-part of Ser. No. 706,315, Jul. 19, 1976, abandoned, which is a continuation-in-part of Ser. No. 579,766, May 22, 1975, abandoned, which is a continuation-in-part of Ser. No. 530,791, Dec. 9, 1974, abandoned.

[51] Int. Cl.$^2$ .................................. C07C 23/18
[52] U.S. Cl. ........................................ 260/648 F
[58] Field of Search ............................ 260/648 F

[56] References Cited

U.S. PATENT DOCUMENTS

| | | | |
|---|---|---|---|
| 3,641,167 | 2/1972 | Moore et al. | 260/648 F |
| 4,041,086 | 8/1977 | Moore et al. | 260/648 F |
| 4,143,079 | 3/1979 | Moore | 260/648 F |

*Primary Examiner*—C. Davis
*Attorney, Agent, or Firm*—J. Edward Hess; Donald R. Johnson; Stanford M. Back

[57] ABSTRACT

Perfluorinated polycyclic hydrocarbons may be produced in high yield by a three-stage process comprising contacting a cyclic hydrocarbon such as an alkyladamantane with a fluoride of silver, manganese, sulfur or the like under varying reaction conditions, generally in the liquid state, to provide a partially fluorinated cyclic hydrocarbon. This fluorination is followed by a second stage vapor phase reaction with a fluoride of cobalt or the like at temperatures generally just above the boiling point of the material to yield highly fluorinated cyclic compounds, followed by a third stage reaction with the same reagent at substantially higher temperatures to provide the desired perfluorinated material. Alternatively, the partially fluorinated material for use in the second stage may be derived from known sources, using any known partially fluorinated cyclic hydrocarbon.

In a further embodiment, a fluidized bed reactor may be substituted for the second and third vapor phase stages described above.

42 Claims, No Drawings

CYCLIC HYDROCARBON PERFLUORINATION PROCESS

CROSS-REFERENCE TO RELATED CASES

This application is a continuation-in-part of Ser. No. 968,942, filed Dec. 13, 1978, which in turn is a continuation of Ser. No. 898,058, filed Apr. 20, 1978, which in turn is a continuation-in-part of Ser. No. 771,873, filed Feb. 25, 1977, which in turn is a continuation-in-part of Ser. No. 706,315, filed July 19, 1976, which in turn is a continuation-in-part of Ser. No. 579,766, filed May 22, 1975, which in turn is a continuation-in-part of Ser. No. 530,791, filed Dec. 9, 1974 all of which are now abandoned.

BACKGROUND OF THE INVENTION

This invention relates to an improved process for the fluorination of polycyclic hydrocarbons. More particularly, this invention relates to an improved method for the fluorination, preferably perfluorination, of said hydrocarbons using a three-stage reaction which effectively eliminates the production of unwanted by-products.

U.S. Pat. No. 3,641,167, as well as copending application Ser. No. 647,944, filed Jan. 12, 1976 and now U.S. Pat. No. 4,041,086, discloses a one-stage method for making perfluoroalkyladamantanes. Recent data using new analytical techniques now show that under the reaction conditions employed therein, using $CoF_3$ alone and high temperature, degradation of the non-fluorinated hydrocarbon cyclic structure does result, with the formation of ring-opened products.

SUMMARY OF THE INVENTION

In accordance with the present invention, it has now been found that polycyclic hydrocarbons, or, with certain reagents, the carbonyl derivatives thereof, or, if necessary, their hydroxylated chlorinates, or brominated derivatives, may be perfluorinated with substantially no degradation of the cyclic structure by (1) partially fluorinating the starting cyclic compound with a mild fluorinating agent other than $CoF_3$ under moderate conditions in a first stage, followed by (2) reacting said partially fluorinated material in a second stage in the presence of a strong fluorinating agent at temperatures just above the boiling point of said material to provide a highly fluorinated compound; and thereafter (3) either passing said highly fluorinated compound into a separate reactor, or recycling it into the same second stage reactor, at considerably higher temperatures to provide an essentially perfluorinated polycyclic hydrocarbon free of any degradation ring-opened products.

DESCRIPTION OF THE INVENTION

The starting materials for this improved perfluorination process comprise non-aromatizable polycyclic hydrocarbons selected from the group consisting of alkyladamantanes, as described in U.S. Pat. No. 3,641,167, and having from 11–30 carbon atoms, preferably 12–14 carbon atoms, such as 1,3-dimethyladamantane, 1,3,5-trimethyladamantane, 1-ethyladamantane, 1-methyladamantane, 1-ethyl-3-methyladamantane, 1-ethyl-3,5-dimethyladamantane, or the like; endo- and exo-tetrahydrodicyclopentadiene; methanodecalins such as 1,4-methanodecalin or 1,4,5,8-dimethanodecalin; hydrogenated pinene, camphane; bicycloheptanes; bicyclooctane; bicyclononanes; and the like. When these compounds are treated in accordance with the process of this invention, there are obtained the corresponding perfluorinated polycyclic materials in high yield and purity, wherein at least 95% of the hydrogen atoms, and more preferably 97% to 100%, are replaced by fluorine atoms. Generally, with this improved process, the conversion of the starting material to the corresponding perfluorinated compound is at least 50%, and most usually about 90% or more.

These perfluorinated materials are useful in a variety of industrial and pharmaceutical applications. The fluorinated alkyladamantanes, for example, are useful as gas turbine engine coolants, dielectric coolants for transformers, generators, and the like, as well as components in synthetic blood compositions, perfusion media, and like biological applications. The perfluorinated cyclic materials are also useful as working fluids in heat pipes and Rankin cycle engines.

The first stage of the aforedescribed process to provide a partially fluorinated intermediate is conveniently carried out by contacting the polycyclic hydrocarbon or its hydroxylated, chlorinated, brominated, or carbonylated derivatives, depending on the fluorinating agent used, in the liquid phase with a fluorinating agent selected from the group consisting of HF, HF-pyridine complex, $AgF_2$, $MnF_3$, $SF_4$, $SbF_5$, $KCoF_4$, and fluoro olefins, under varying conditions of temperature, pressure, and the like, depending upon the nature of the starting material and fluorinating agent employed. These fluorinating agents are much milder in their action than $CoF_3$ on hydrocarbons. Consequently, the degree of fluorination can be controlled by the proper selection of agent and starting material. Generally, the incorporation of from about 3 to 6 fluorine atoms into the hydrocarbon is found to stabilize the material for the subsequent more severe conditions employed in exhaustive fluorination with e.g. $CoF_3$.

In general, in this first, partial fluorination stage the above-mentioned mild fluorinating agents may be reacted directly with the polycyclic hydrocarbons per se, or their partly chlorinated or brominated derivatives, if desired. However, one exception to this is the reaction of these compounds with $SF_4$ or dialkylaminosulfur fluorides, in which case the cyclic starting material must first be carbonylated before it can satisfactorily react with $SF_4$ or dialkylaminosulfur fluoride. Thus, for example, in the case of the alkyladamantanes these compounds must first be converted to their corresponding ketones, aldehydes, acids, or hydroxy derivatives before they will properly react with the $SF_4$ or dialkylaminosulfur reagent.

Illustrations of the methods for forming these adamantyl carbonyl derivatives can be found, for example, in the teachings of U.S. Pat. Nos. 3,356,740 and 3,356,741 (adamantyl ketone and diketone derivatives); U.S. Pat. Nos. 3,250,805, 3,356,718 and 3,356,709 (adamantyl dihydroxides and dicarboxylic acids). Other like methods will be recognized and understood by those skilled in the art.

Similarly, other such carbonylated polycyclic starting materials can be prepared in accordance with similar known techniques.

It will thus be understood from the foregoing that a general recitation of the partial (i.e., first stage) fluorination of the polycyclic starting materials is in all cases intended to include their carbonyl derivatives when SF$_4$ or dialkylaminosulfur fluorides is used as the fluorinating agent.

In addition to the use of carbonyl derivatives of cyclic materials to be perfluorinated when SF$_4$ is used, is the use of analogous known alcohol derivatives of these compounds when HF or HF-pyridine complex is the partial fluorinating agent; and chlorinated or brominated derivatives where SbF$_5$ is employed.

Also, cyclic dienes such as 1,3-cyclohexadiene may be reacted with fluoroolefins such as hexafluoro-propene in a Diels-Alder type reaction, to obtain partially fluorinated polycyclic hydrocarbons, as described in more detail below. These materials may then also be perfluorinated in accordance with this invention.

Thus, these aforedescribed Diels-Alder reaction products are also intended to be included in the general definition of the partially fluorinated polycyclic hydrocarbons which may then be perfluorinated with, e.g., CoF$_3$ as described above.

It will thus be evident from the foregoing description that it is within the scope of this invention to exhaustively fluorinate with a strong fluorinating agent a partially fluorinated, and thus stabilized, cyclic hydrocarbon which has been prepared by any mild fluorination technique.

The amount of fluorination necessary to impart ring structure stability to the polycyclic materials prior to their reaction with strong fluorinating agents such as CoF$_3$ in the second and third stages of this process is not critical but desirably should comprise the replacement of from about 3-6 hydrogen atoms by fluorine atoms up to as much as a 50% replacement of such hydrogen by fluorine. The location of these fluorine atoms may be either in the nucleus or the side chain of the hydrocarbon molecule, or both. Accordingly, it will be understood that the product of the first stage fluorination may comprise either a single partially fluorinated product, or a mixture of partially fluorinated materials depending upon the fluorinating agent employed. This product, prior to contact with CoF$_3$ or the like, in the next stage, should first be separated from the first fluorinating agent, preferably by distillation.

In the second stage of this process, the object is to achieve as high a degree of fluorination as possible short of degrading the ring structure of the compound. The effect of this fluorination step is to impart a much greater stability to the partially fluorinated polycyclic material in order that, in the last stage, virtually 100% perfluorination can be achieved under much more stringent reaction conditions without forming ring degradation by-products. This high degree of fluorination, in the second stage, which generally falls short of perfluorination by not more than about 1-25%, is readily accomplished by contacting the partially fluorinated hydrocarbon mixture with CoF$_3$ in the vapor phase (by preheating) at a moderate charge rate at temperatures ranging from just above the boiling point of the charge materials to about 50° C. above its boiling point. Preferably, a multi-zone reactor with temperatures graduated from just above boiling point to 50° C. above should be used. Since the reaction is an exothermic one, care should be taken to control the temperature within about these ranges in order to avoid degrading the molecules.

The final stage, which likewise is in the vapor phase, comprises either recycling the highly fluorinated product of the CoF$_3$ reaction back into the same reactor, or passing it into a separate reactor, which is heated to a considerably higher temperature than the second stage, preferably about 100° C. greater across the thermally graded reactor, to achieve substantially complete perfluorination, and provide yields of about 50-95%, based on the amount of original charge stock.

The perfluorinated product is then desirably cooled to temperatures of from about 0° C. to −80° C. by passing it through several cooling traps as it is removed from the reactor in order to collect not only the product, but also HF and any othergaseous products.

In a further embodiment of this invention, it has been found that the second and third stage of the aforedescribed process, both of which are carried out in the vapor phase, may be replaced by one or more stages comprising a fluidized bed of CoF$_3$. Generally, it has been found that a single pass through such a fluidized bed reactor will achieve the same results as the last two stages of the above vapor phase reactors, and thus comprises an improvement of said process.

In carrying out said improvement, the partially fluorinated material from the first zone is passed through a fluidized bed of CoF$_3$, preferably in a continuous manner, at a charge rate of 2-3 lbs/hr. wherein said bed is maintained at a temperature of 325°-425° C., preferably at 350°-375° C. Simultaneously, for purposes of regenerating the CoF$_3$, fluorine gas may be passed through the CoF$_3$ suspended solids to maintain the CoF$_3$ in a valency state which is capable of perfluorinating the organic feed. If desired, the fluorine gas may be diluted with inert gases such as nitrogen.

The CoF$_3$ particles should preferably be maintained in a suspended, fluidized state by means of mechanical mixers, although inert gases may be used for this purpose if desired. Also if desired, the CoF$_3$ particles may be admixed with inert solids to act as heat carriers and facilitate heat exchange. The perfluorinated product is then withdrawn and recovered.

The invention will now be illustrated by the following examples.

The following four examples demonstrate the preparation of partially fluorinated adamantanes which may then be perfluorinated in accordance with the process of this invention.

EXAMPLE 1

Adamantane dicarboxylic acid (22.4 g-0.1 mole) and SF$_4$ (27.0 g-25% excess) were heated in a hoke bomb for 24 hours at 110° C. The contents of the pressure vessel were cooled, extracted with CCl$_4$, filtered and the CCl$_4$ evaporated off. The residue consisted of 21.8 g of bis(-trifluoromethyl) adamantane (80% yield).

In a like manner, when adamantane carboxylic acid was heated with SF$_4$, there was obtained trifluoromethyl adamantane.

EXAMPLE 2

2-Adamantanone (15.0 g-9.1 mole) and SF$_4$ (13. g-25% excess) were heated as in Example 1. The product was worked up as described in Example 1 to give 12.9 g of 2,2-difluoro adamantane (75% yield).

EXAMPLE 3

5,7-dimethyl-1,3-adamantane dicarboxylic acid (25.2 g-0.1 mole) and SF$_4$ (27.0 g-25% excess) were heated and worked up as in Example 1 to give 18 g of 1,3-bis(-trifluoromethyl)-5,7-dimethyl adamantane (60%).

EXAMPLE 4

1,3-dimethyl adamantane (42 g) is added slowly to a slurry of MnF$_3$ (1 lb) in perfluoro 1-methyl decalin. After all the hydrocarbon has been added the mixture is heated with rapid stirring to 200° C. for 24 hours, and the product extracted with Freon 113 and distilled to remove both the Freon 113 and perfluoro 1-methyl decalin. The distillation residue consists of partially fluorinated 1,3-dimethyl adamantane in which the average molecule contains approximately 8 fluorine atoms; e.g., C$_{12}$H$_{12}$F$_8$.

EXAMPLE 5

Bistrifluoromethyl adamantane (24 cc; 33.67 g; 0.123 moles) from Example 1 was charged into a preheater at 0.247 cc/min/ The preheater temperature was 250° C., and the CoF$_3$ reactor temperature was graduated from 250° C. in Zone 1 to 300° C. in Zone 4. The product line was kept at 225° C. After all the hydrocarbon had been charged to the reactor, the reactor was purged with nitrogen for 3.25 hours. The crude product weighed 46.0 g. This material was water washed until the pH of the water was 5.

This material from the second stage was dried over mole sieves overnight and then 45.84 g was recharged at a rate of 0.764 cc/min. to the reactor which was graduated from 275° C. in Zone 1 to 380° C. in Zone 4 for the final stage. The reactor was purged with nitrogen for 4 hours before removing the product receiver containing 47.8 g. fluorocarbon; 75% material balance G.C. analysis showed the product contained 90% perfluoro 1,3-dimethyl adamantane, confirmed by mass spectrography and $^{19}$FNMR.

When the trifluoromethyl adamantane of Example 1 was treated in a similar manner and worked up there was recovered perfluoro 1-methyl adamantane.

A similar run was made with 1,3-bis(trifluoromethyl)-5, 7-dimethyl adamantane of Example 3 to give a 55% yield of perfluoro tetramethyl adamantane.

In a similar fashion 2,2-difluoro adamantane of Example 2 was reacted with CoF$_3$ in accordance with the procedures of Example 5 to give the corresponding perfluoroadamantane in high purity and yield.

EXAMPLE 6

The following example illustrates the results obtained when the first (partial) fluorination stage of this invention is not employed:

Exo-tetrahydrodicyclopentadiene (25 cc:24.15 g; 0.1776 moles) was charged into a preheater at 0.494 cc/min. The preheater temperature was 225° C., and the CoF$_3$ reactor temperature was graduated from 200° C. in Zone 1 to 250° in Zone 4. The product line was kept at 225° C. After all the hydrocarbon had been charged to the reactor, the reactor was purged with nitrogen for 3.25 hours. The crude product weighed 63.6 g. This material was water washed until the pH of the water was 5.

The material from the first stage was dried over mole sieves overnight and then 55.84 g was recharged at a rate of 0.764 cc/min. to the reactor which was graduated from 300° C. in Zone 1 to 375° C. in Zone 4 for the final stage. The reactor was purged with nitrogen for 4 hours before removing the product receiver containing 60.8 g fluorocarbon; 87% material balance based on the 24.15 g of THDCP charged. G.C analysis showed the product contained 40% of endo- and exo-perfluoro-tetrahydrodicyclopentadiene, 45% of perfluoro bicyclo [5.3.0.] decane and 15% unknown fluorocarbons.

EXAMPLE 7

Exo-tetrahydrodicyclopentadiene (35 g) is added slowly to a slurry of MnF$_3$ (1 lb) in perfluoro 1-methyl decalin solvent. After all the hydrocarbon has been added, the mixture is heated to 200° C. and stirred rapidly for 24 hours. The product is extracted with Freon 113 and distilled to remove both the Freon 113 and perfluoro 1-methyl decalin. The distillation residue consists of partially fluorinated tetrahydrodicyclopentadiene in which the average molecule contains approximately 7 fluorine atoms: C$_{10}$H$_9$F$_7$.

When the thus obtained partially fluorinated tetrahydrodicyclopentadiene is then perfluorinated with CoF$_3$ in accordance with the procedures of Example 5, there is obtained substantially pure exo- and endo-perfluorotetrahydrodicyclopentadiene in high yield, which is essentially free of any of the by-products enumerated in Example 6.

EXAMPLE 8

In accordance with the procedures of Example 7, but substituting partially fluorinated camphane, hydrogenated pinene, 1,4-methanodecalin or 1,4,5,8-dimethanodecalin for partially fluorinated tetrahydrodicyclopentadiene, there is obtained the corresponding perfluorinated cyclocarbon in high yield, and substantially free of any degradation ring-opened by-products.

EXAMPLE 9

As indicated above, fluoroolefins and acetylenes, for example, readily undergo Diels-Alder type reactions to function as dienophiles in 1,4-cyclo-addition reactions; their reactivity towards dienes is generally higher than that of their hydrocarbon analogues. The following examples demonstrate the preparation of partially fluorinated cyclocarbons which may then be exhaustively fluorinated in accordance with the procedures of Example 5 to provide perfluorocyclocarbons in high yield and essentially free of ring-opened by-products:

A. Reaction of cyclopentadiene with hexafluorobut-2-yne at 100° C. for 24 hours gives 2,3-bis(trifluoromethyl)bicyclo [2.2.1] heptadiene which, upon hydrogenation over platinum, gives 2,3-bis(trifluoromethyl)bicyclo [2.2.1] heptane.

B. In a like manner, octafluoro-but-2-ene and cyclopentadiene react to give 2,3-difluoro-2,3-bis(trifluoromethyl) bicyclo [2.2.1] heptane which, after hydrogenation over ruthenium gives 2,3-bis(trifluoromethyl)bicyclo [2.2.1] heptane.

It should be noted, however, that one exception to this above perfluorination method was found when thermally unstable 2-(trifluoromethyl) 2,3,3-trifluorobicyclo [2.2.2] octane and its corresponding bis(trifluoromethyl)bicyclo [2.2.2] octane, i.e., partially fluorinated lower alkyl- or lower di-alkyl-substituted bicyclooctanes were perfluorinated. Because of the thermal instability of their particular ring structure, it was discovered that substantial monocyclic perfluorinated products were recovered in the reaction mixture, rather than pure bicyclic compounds.

Thus, for example, when 2-(trifluoromethyl) 2,3,3-trifluoro-bicyclo [2.2.2] octane, which was prepared by reacting 1,3-cyclohexadiene with hexafluoropropene, followed by hydrogenation with a catalyst such as rhodium, as described above, was perfluorinated in accordance with this process, substantial amounts of perfluoro-n-propylcyclohexane and perfluoro-isopropylcyclohexane were recovered, together with measurable amounts of unidentified perfluorinated materials.

Similarly, when bis(trifluoromethyl) bicyclo [2.2.2] octane was perfluorinated in this manner, there was recovered a reaction mixture containing perfluorodimethylcyclohexane, tetrafluoroethylene, and a mixture of unidentified $C_{10}F_{20}$ materials.

Thus, those skilled in the art will understand that in the case of the thermally unstable partially fluorinated lower alkyl- and lower dialkyl-substituted bicyclooctanes, perfluorination under the conditions defined herein lead to at least partial ring-opening of said bicyclooctanes.

EXAMPLE 10

Norbornadiene (1 mole) and a 25% molar excess of hexafluorocyclopentadiene are heated for 24 hours at 100° C. to give

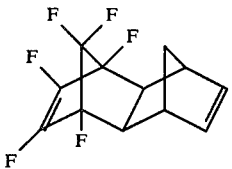

which, after treatment with $CoF_3$ in accordance with the procedures of Example 5 yields highly pure perfluoro 1,4,5,8-dimethanodecalin.

EXAMPLE 11

2.5 lbs/hr. of tetrahydrodicyclopentadidne, and 11.3 lbs/hr. fluorine are fed at a steady rate for 5 hours to a mechanically stirred fluidized bed of $CoF_3$ which is maintained at 375° C. The product (36 lbs) is a 50:50 mixture by weight of perfluoro-tetrahydrodicyclopentadiene and perfluoro-bicyclo [5.3.0] decane.

In accordance with the foregoing procedure, but substituting 2.5 lbs/hr. of 1,3-bistrifluoromethyl adamantane and 3.4 lbs/hr. of fluorine, there is obtained 20 lbs of perfluoro-1,3-dimethyladamantane after 5 hours, together with small amounts of lesser fluorinated by-products.

The invention claimed is:

1. A process for the perfluorination of non-aromatizable polycyclic hydrocarbons which comprises:
   (A) partially fluorinating a polycyclic hydrocarbon or a carbonyl, hydroxyl, chlorinated, or brominated derivative thereof, by contacting it in a first reaction zone with a fluorinating agent selected from the group consisting of HF, HF-pyridine, $AgF_2$, $MnF_3$, $SF_4$, $SbF_5$, $KCoF_4$ and fluoroolefins, in the liquid phase under conditions sufficient to provide not more than about 50% fluorination corresponding to perfluorination;
   (B) further fluorinating said partially fluorinated polycyclic hydrocarbon in the vapor phase in a second reaction zone with $CoF_3$ at a temperature of no greater than about 50° C. above the boiling point of the fluorinated material to provide a highly fluorinated material having a degree of fluorination corresponding to no more than about 75-95% of perfluorination; and
   (C) thereafter contacting said highly fluorinated material with $CoF_3$ in the vapor phase at temperatures about 100° C. higher than were first employed in (B) above, to provide a substantially perfluorinated polycyclic hydrocarbon.

2. The process according to claim 1 wherein step (C) comprises recycling said highly fluorinated material from said second reaction zone back to said second reaction zone to contact the same with $CoF_3$ at temperatures about 100° C. higher than were first employed in said second reaction zone.

3. The process according to claim 1 wherein the temperature in the first reaction zone ranges from about 175° to 350° C.

4. The process according to claim 1 wherein the temperatures in step (B) are graduated from just above the boiling point of the recycled material in the first part of the second reaction zone to about 50° C. above said boiling point in the last part of said reaction zone.

5. The process according to claim 1 wherein the temperatures in step (C) are graduated from about 100° C. above the boiling point of the highly fluorinated material in the first part of said further reaction zone to about 150° C. above said boiling point in the last part of said reaction zone.

6. The process according to claim 1 wherein the polycyclic hydrocarbon is an alkyladamantane having from 11 to 30 carbon atoms.

7. The process according to claim 6 wherein the fluorinating agent in the first reaction zone is $SF_4$ and the alkyladamantane is in the form of a carbonylated derivative thereof.

8. The process according to claim 6 wherein the alkyladamantane is 1-ethyladamantane, 1-methyladamantane, 1-ethyl-3-methyladamantane, 1-ethyl-3,5-dimethyladamantane.

9. The process of claim 6 wherein the alkyladamantane is 1,3-dimethyladamantane.

10. The process according to claim 7 wherein the alkyladamantane is adamantane carboxylic acid, adamantane dicarboxylic acid or 5,7-dimethyl-1,3-adamantane dicarboxylic acid.

11. The process according to claim 7 wherein the alkyladamantane is adamantanone.

12. The process according to claim 1 wherein the polycyclic hydrocarbon is a bicycloheptane or bicyclononane.

13. The process according to claim 1 wherein the polycyclic hydrocarbon is exo-tetrahydrodicyclopentadiene.

14. The process according to claim 1 wherein the polycyclic hydrocarbon is a methanodecalin, camphane, or hydrogenated pinene.

15. A process for the perfluorination of non-aromatizable polycyclic hydrocarbons which comprises:
   (A) fluorinating a partially fluorinated polycyclic hydrocarbon in the vapor phase with $CoF_3$ in a reaction zone at a temperature of no greater than about 50° C. above the boiling point of the fluorinated material to provide a highly fluorinated material having a degree of fluorination corresponding to no more than about 75-95% of perfluorination; and
   (B) recovering and passing said highly fluorinated material to a further reaction zone to contact the same with $CoF_3$ in the vapor phase at temperatures about 100° C. higher than were first employed, to provide a substantially perfluorinated polycyclic hydrocarbon.

16. The process of claim 15 wherein step (B) comprises recycling said highly fluorinated material from step (A) back to the reaction zone to contact the same with $CoF_3$ at temperatures about 100° C. higher than were first employed in step (A).

17. The process according to claim 15 wherein the temperature in step (A) is graduated from just above the boiling point of the charge material in the first part of said reaction zone to about 50° C. above said boiling point in the last part of said reaction zone.

18. The process according to claim 15 wherein the temperatures in step (B) are graduated from about 100° C. above the boiling point of the highly fluorinated material in the first part of said reaction zone to about 150° C. above said boiling point in the last part of said reaction zone.

19. The process according to claim 15 wherein the partially fluorinated hydrocarbon is a partially fluorinated adamantane.

20. The process according to claim 15 wherein the partially fluorinated hydrocarbon is a partially fluorinated tetrahydrodicyclopentadiene.

21. The process according to claim 15 wherein the partially fluorinated hydrocarbon is a partially fluorinated bicyclononane.

22. The process according to claim 15 wherein the partially fluorinated hydrocarbon is a partially fluorinated methanodecalin, camphane, or hydrogenated pinene.

23. The process according to claim 19 wherein the partially fluorinated adamantane is trifluoromethyl adamantane, bis(trifluoromethyl)adamantane, 1,3-bis(trifluoromethyl)-5,7-dimethyl adamantane.

24. The process according to claim 19 wherein the partially fluorinated adamantane is partially fluorinated 1,3-dimethyladamantane.

25. A process for the perfluorination of non-aromatizable polycyclic hydrocarbons which comprises:
(A) partially fluorinating a polycyclic hydrocarbon or the carbonyl, hydroxyl, chlorinated or brominated derivative thereof, by contacting it in a first reaction zone with a fluorinating agent selected from the group consisting of HF, HF-pyridine, $AgF_2$, $MnF_3$, $SF_4$, $SbF_5$, $KCoF_4$ and fluoroolefins, in the liquid phase under conditions sufficient to provide not more than about 50% fluorination corresponding to perfluorination; and
(B) thereafter further fluorinating said partially fluorinated polycyclic hydrocarbon in the vapor phase in a second reaction zone with $CoF_3$ at a temperature of no greater than about 50° C. above the boiling point of the fluorinated material to provide a highly fluorinated material having a degree of fluorination corresponding to about 75–95% of perfluorination.

26. The process according to claim 25 wherein the temperature in the first reaction zone ranges from about 175° to 350° C.

27. The process according to claim 25 wherein the temperature in step (B) is graduated from just above the boiling point of the recycled material in the first part of the second reaction zone to about 50° C. above said boiling point in the last part of said reaction zone.

28. The process according to claim 25 wherein the polycyclic hydrocarbon is an alkyladamantane having from 11 to 30 carbon atoms.

29. The process according to claim 28 wherein the fluorinating agent in the first reaction zone is $SF_4$ and the alkyladamantane is in the form of a carbonylated derivative thereof.

30. A process for the perfluorination of non-aromatizable polycyclic hydrocarbons which comprises:
(A) Partially fluorinating a polycyclic hydrocarbon or a carbonyl, hydroxyl, chlorinated, or brominated derivative thereof, by contacting it in a first reaction zone with a fluorinating agent selected from the group consisting of HF, HF-pyridine, $AgF_2$, $MnF_3$, $SF_4$, $SbF_5$, $KCoF_4$ and fluoroolefins, in the liquid phase under conditions sufficient to provide not more than about 50% fluorination corresponding to perfluorination;
(B) thereafter passing said partially fluorinated hydrocarbon through a fluidized bed of $CoF_3$ in the presence of fluorine gas at an elevated temperature, and recovering a substantially perfluorinated polycyclic hydrocarbon.

31. The process of claim 30 wherein the temperature of the fluidized bed is in the range of 325°–425° C.

32. The process of claim 30 wherein the charge rate of the partially fluorinated hydrocarbon into the fluidized bed is about 2–3 lbs/hr.

33. The process of claim 30 wherein the fluidized bed is maintained with mechanical stirrer.

34. The process according to claim 30 wherein the polycyclic hydrocarbon is an alkyladamantane having from 11 to 30 carbon atoms.

35. The process according to claim 34 wherein the fluorinating agent in the first reaction zone is $SF_4$ and the alkyladamantane is in the form of a carbonylated derivative thereof.

36. The process according to claim 34 wherein the alkyladamantane is 1-ethyladamantane, 1-methyladamantane, 1-ethyl-3-methyladamantane, 1-ethyl-3,5-dimethyladamantane.

37. The process of claim 34 wherein the alkyladamantane is 1,3-dimethyladamantane.

38. The process according to claim 36 wherein the alkyladamantane is adamantane carboxylic acid, adamantane dicarboxylic acid or 5,7-dimethyl-1,3-adamantane dicarboxylic acid.

39. The process according to claim 36 wherein the alkyladamantane is adamantanone.

40. The process according to claim 30 wherein the polycyclic hydrocarbon is a bicycloheptane or bicyclononane.

41. The process according to claim 30 wherein the polycyclic hydrocarbon is exo-tetrahydrodicyclopentadiene.

42. The process according to claim 30 wherein the polycyclic hydrocarbon is a methanodecalin, camphane, or hydrogenated pinene.

* * * * *